United States Patent [19]

Van der Knaap

[11] Patent Number: Plant 6,869

[45] Date of Patent: Jun. 20, 1989

[54] CHRYSANTHEMUM PLANT NAMED WALL STREET

[75] Inventor: Jacques C. M. Van der Knaap, De Lier, Netherlands

[73] Assignee: Fides Beheer, De Lier, Netherlands

[21] Appl. No.: 124,549

[22] Filed: Nov. 23, 1987

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

An anemone type Chrysanthemum named Wall Street, having a unique combination of essentially pure white mature ray floret color and a large disc cushion which at maturity is a dark pink or red, with a very dark red center. The combination of the large, dark pink-red cushion with the white ray florets is unique and highly attractive.

1 Drawing Sheet

The present invention comprises a new and distinct cultivar of *Chrysanthemum morifolium,* hereinafter referred to by the cultivar name Wall Street.

Wall Street is a product of a planned breeding program which had the objective of creating new Chrysanthemum cultivars having single capitulum type, pink-white ray florets, dark pink flower center, low temperature tolerance, and the ability to produce commercially acceptable quality in year around cut mum programs. Such traits in combination were not present or needed improvements in previously available commercial cultivars.

Wall Street was originated from a hybridization made by applicant in a controlled breeding program in De Lier, Holland in 1984. The female parent was Lireley, an unpatented and non-commercial variety. The male parent of Wall Street was Penny Lane, a cultivar of applicant disclosed in a pending application.

Wall Street was discovered and selected as one flowering plant within the progeny of the stated parentage by Jacques C. M. Van der Knaap in September 1984 in a controlled environment in De Lier, Holland.

The first act of asexual reproduction of Wall Street was accomplished when vegetative cuttings were taken from the initial selection in November 1984 in a controlled environment in De Lier, Holland by a technician working under formulations established and supervised by Jacques C. M. Van der Knaap. Horticultural examination of selected units initiated in April 1985 has demonstrated that the combination of characteristics as herein disclosed for Wall Street are firmly fixed and are retained through successive generations of asexual reproduction.

Wall Street has not been observed under all possible environmental conditions. The phenotype may vary significantly with variations in environment such as temperature, light, intensity, and day length. The following observations, measurements and comparisons describe plants grown in De Lier, Holland under greenhouse conditions which approximate those generally used in commercial practice.

The following traits have been repeatedly observed and are determined to be basic characteristics of Wall Street, which in combination distinguish this Chrysanthemum as a new and distinct cultivar:

1. Flat capitulum form.
2. Anemone flower type.

3. Pink-white ray florets, with dark pink disc cushion, producing an extremely attractive inflorescence.
4. Diameter across the face of the capitulum 55–65 mm.
5. Dark pink or red (immature) disc florets which become somewhat lighter pink-red at maturity, with the peripheral discs turning white to yellow.

Of the many commercial cultivars known to the present inventor, the most similar in comparison to Wall Street is Penny Lane, disclosed in a pending application of applicant. In comparison to Penny Lane, Wall Street has more vigor, a longer response time, smaller and darker green leaves, and a darker and substantially larger disc floret area of red-pink color. The capitulum form and capitulum type are similar to those same characteristics of Penny Lane.

The accompanying photographic drawing shows in perspective view the typical inflorescence and foliage characteristics of Wall Street, with colors being as nearly true as possible with illustrations of this type.

In the following description, color references are made to The Royal Horticultural Society Colour Chart. The color values were determined between 11:00–12:00 a.m. in June 1986 under natural daylight at De Lier, Holland.

Classification:

*Botanical.*—Chrysanthemum morifolium, Ramat., cv. Wall Street.

*Commercial.*—Cut daisy spray.

INFLORESCENCE

A. Capitulum:

*Form.*—Flat

*Type.*—Daisy

*Diameter across face.*—55–65 mm

B. Corolla of ray florets:

*Color (general tonality from a distance of three meters)*—Pinkish white with red-pink center.

*Color (upper surface).*—Under conditions of high light such as late spring in the Netherlands (when the photographic drawing was taken) immature florets are infused with reddish tones of color ranging from 183A to 186*A, with the tinging decreasing but still evident and becoming lighter in color when the flowers are fully open;*

*under low light conditions, little or no tinging occurs and the ray florets are essentially white.*

C. Corolla of disc florets:

*Color* (*mature*).—Center remains dark, approximately 60A-B, with gradual lightening towards periphery, with 60C and 60D appearing; edge of disc cushion approaches white, and a few yellow disc florets are also present at the periphery of the cushion.

*Color* (*immature*).—Dark red-purple 60A-B, with some lightening at periphery.

D. Reproductive organs:

*Androecium.*—Present only in disc florets; numerous.

*Gynoecium.*—Present in both disc and ray florets, numerous.

PLANT

A. General appearance:

*Height.*—80 cm.

B. Foliage:

*Color* (*upper surface*).—137A.

*Color* (*under surface*).—137C.

*Shape.*—Margins deeply indented.

I claim:

1. A new and distinct cultivar of Chrysanthemum plant named Wall Street, as described and illustrated, and parts thereof.

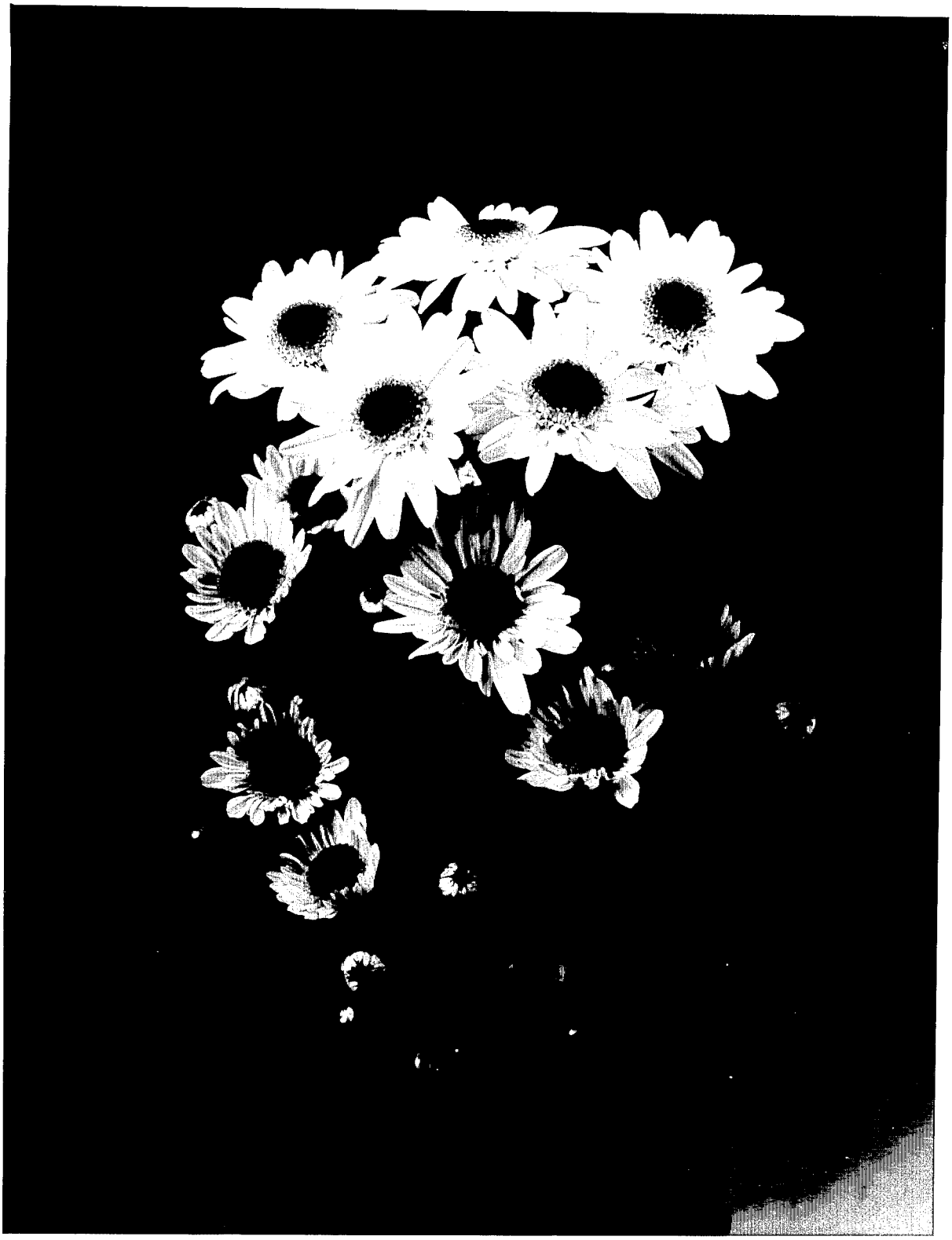

* * * * *